US008257054B2

(12) United States Patent
Voltenburg, Jr. et al.

(10) Patent No.: US 8,257,054 B2
(45) Date of Patent: Sep. 4, 2012

(54) METHOD OF INSTALLING AND REMOVING A CASSETTE FROM A PUMP BODY HAVING A MOUNTING PIN

(75) Inventors: Robert R. Voltenburg, Jr., Davison, MI (US); Loren M. Thompson, Lapeer, MI (US)

(73) Assignee: Curlin Medical Inc., East Aurora, NY (US)

( * ) Notice: Subject to any disclaimer, the term of this patent is extended or adjusted under 35 U.S.C. 154(b) by 0 days.

(21) Appl. No.: 13/069,505

(22) Filed: Mar. 23, 2011

(65) Prior Publication Data

US 2011/0171052 A1 Jul. 14, 2011

Related U.S. Application Data

(62) Division of application No. 11/862,302, filed on Sep. 27, 2007, now Pat. No. 7,934,912.

(51) Int. Cl.
*F04B 43/08* (2006.01)
*F04B 43/12* (2006.01)

(52) U.S. Cl. .............. 417/53; 417/477.2; 417/477.11

(58) Field of Classification Search .............. 417/474, 417/475, 476, 477.1, 477.3, 477.4, 477.5, 417/477.6, 477.7, 477.8, 477.9, 477.11, 477.12, 417/477.13, 477.14, 478, 53
See application file for complete search history.

(56) References Cited

U.S. PATENT DOCUMENTS

| 3,011,684 | A | * | 12/1961 | Corneil ....................... 222/214 |
| 3,597,124 | A | * | 8/1971 | Adams ..................... 417/477.11 |
| 4,708,604 | A | * | 11/1987 | Kidera ...................... 417/477.11 |
| 5,388,972 | A | * | 2/1995 | Calhoun et al. ........... 417/477.11 |
| 5,709,539 | A | * | 1/1998 | Hammer et al. ............ 417/477.3 |
| 5,752,813 | A | * | 5/1998 | Tyner et al. ................ 417/477.2 |
| 2006/0177328 | A1 | * | 8/2006 | Nordell et al. ............. 417/477.2 |

* cited by examiner

*Primary Examiner* — Devon C Kramer
*Assistant Examiner* — Nathan Zollinger
(74) *Attorney, Agent, or Firm* — Hodgson Russ LLP

(57) ABSTRACT

A peristaltic pump assembly includes a pump body including a mounting pin coupled thereto. A removable cassette is slidably received on the mounting pin and is secured to the pump body via a retaining feature. The mounting pin is also configured to allow the removable cassette to rotate into and/or out of an installed position, or to position(s) therebetween.

9 Claims, 3 Drawing Sheets

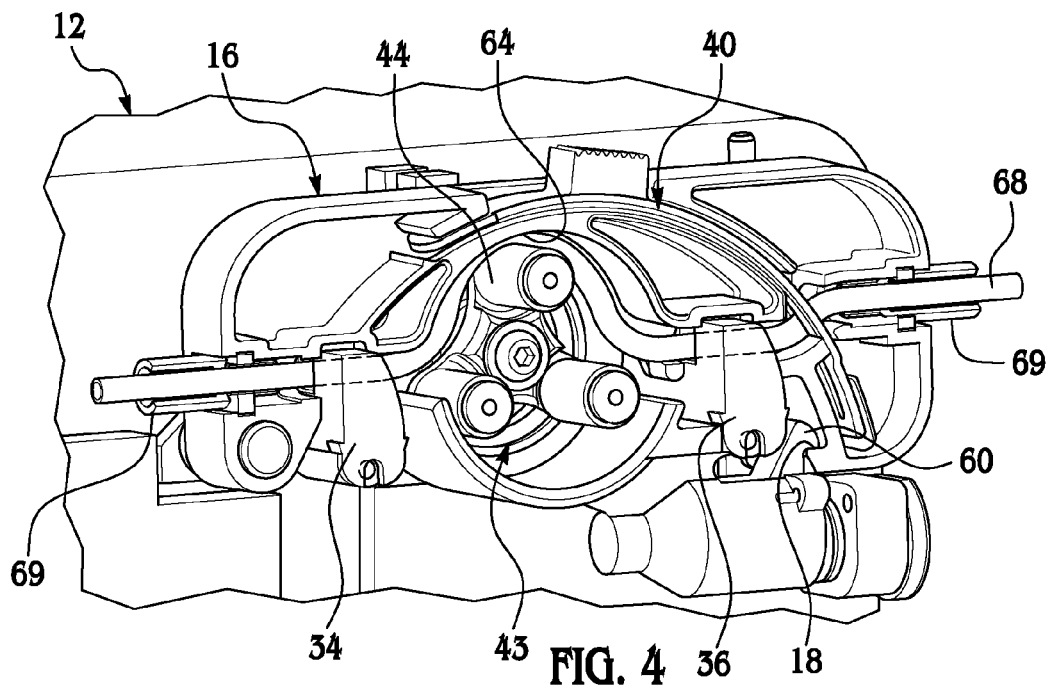
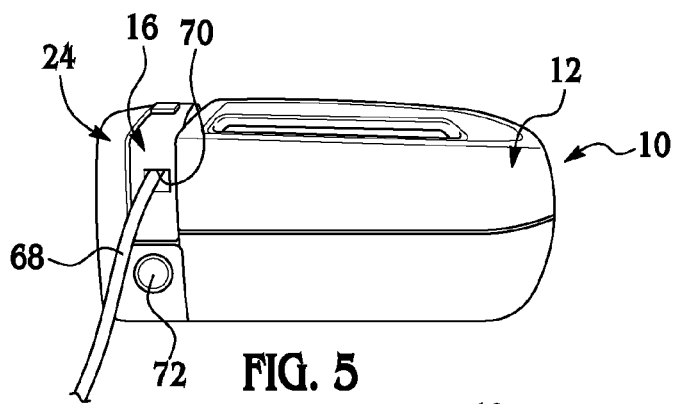
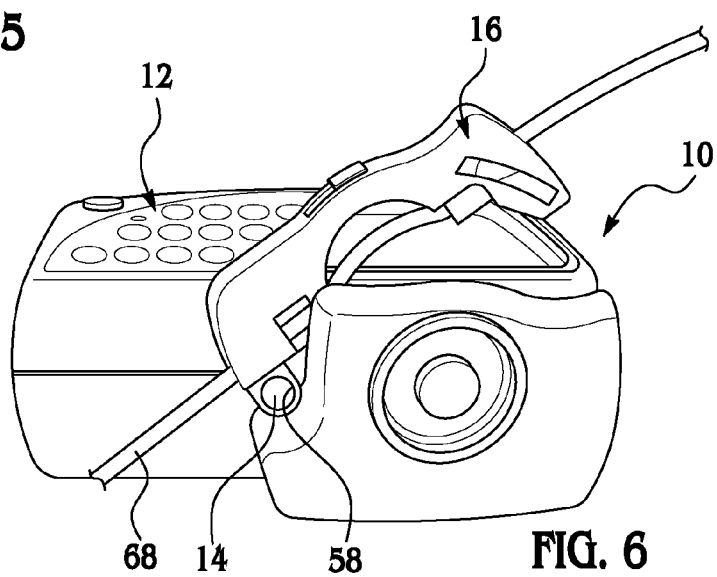

METHOD OF INSTALLING AND REMOVING A CASSETTE FROM A PUMP BODY HAVING A MOUNTING PIN

BACKGROUND

The present disclosure relates generally to peristaltic pump assemblies.

Rotary-style peristaltic pumps often generally include a cassette mounted to and supported by a pump body. In some instances, the pump body includes a cavity formed therein and configured to receive a planetary assembly of rollers. The rollers revolve together when rotationally driven by a drive shaft when the drive shaft is powered by a pump motor.

The cassette generally includes a body having a flexible tube disposed therethrough. When the cassette is mounted to the pump body, the flexible tube surrounds a portion of the assembly of rollers. In response to rotational movement of the rollers, portions of the flexible tube in contact with the rollers compress or otherwise occlude against a wall of the cassette. As a result, fluid traveling through the tube is temporarily trapped in the tube between the occluded points. The trapped fluid is released from the tube when the occlusion force on the tube is released. In this manner, fluid is urged through the tube via peristaltic wave action.

Peristaltic infusion pumps are often used to deliver fluid in a controlled manner, such as, for example, the intravenous delivery of pharmaceutical compositions to a patient. These peristaltic pumps typically use disposable cassettes, where the pump assembly is designed to accommodate the loading of the cassette, as well as the removal of the cassette from the assembly. Such designs, however, may undesirably involve relatively difficult cassette loading and removal schemes.

SUMMARY

A peristaltic pump assembly includes a pump body having a mounting pin coupled thereto. A removable cassette is slidably received on the mounting pin and is secured to the pump body via a retaining feature. The mounting pin is configured to allow the removable cassette to rotate into an installed position, out of an installed position, or to positions therebetween.

BRIEF DESCRIPTION OF THE DRAWINGS

Features and advantages of embodiment(s) of the present disclosure will become apparent by reference to the following detailed description and drawings, in which like reference numerals correspond to similar, though perhaps not identical components. Reference numerals having a previously described function may or may not be described in connection with other drawings in which they appear.

FIG. 4 is a cut-away, perspective view of the peristaltic pump assembly of FIG. 3, including a flexible tubing disposed in the cassette and pump assembly;

FIG. 5 is an end perspective view of the peristaltic pump assembly of FIG. 1; and FIG. 6 is a side perspective view of a pump body, showing the cassette out of the installed position.

DETAILED DESCRIPTION

Embodiment(s) of the peristaltic pump assembly as disclosed herein advantageously provide a simplified pump assembly design to facilitate loading and removal of a cassette to and from a pump body. The mounting and removal processes are relatively simple and efficient, thereby eliminating the need for extensive operator training therefor. The pump assembly enabling the cassette mounting process reduces or substantially eliminates errors with respect to improper positioning of the cassette when assembled with the pump body. Audible and/or tactile feedback may also be available to ensure that the cassette is mounted properly with the pump body. The components of the pump assembly (e.g., the mounting pin) are substantially robust in design to generally withstand long-term wear and use. The pump assembly also advantageously does not require the use of a door, which has a tendency to wear down and/or break from continuous use thereof.

Figure 1:
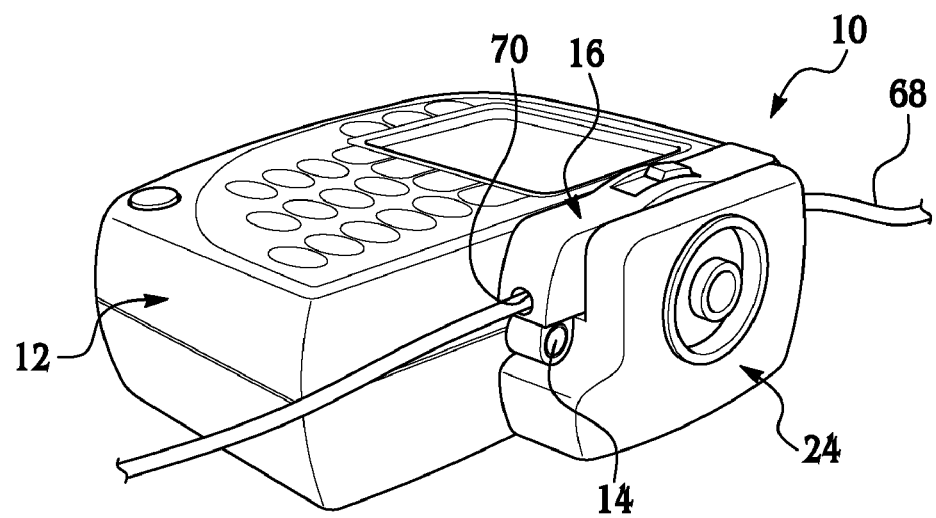
FIG. 1 is a perspective view of an example of a peristaltic pump assembly including an example of a cassette in an installed position.

With reference now to the drawings, FIG. 1 provides a peristaltic pump assembly 10 including a disposable cassette 16 in an installed position. The peristaltic pump assembly 10 includes a pump body 12 with a mounting pin 14 coupled thereto. The cassette 16 is slidably received on the mounting pin 14 and secured to the pump body 12 via a cassette retaining feature 18 (shown in FIGS. 3 and 4). The mounting pin 14 is configured to allow the cassette 16 to rotate into and/or out of the installed position, or to positions therebetween.

Figure 2:
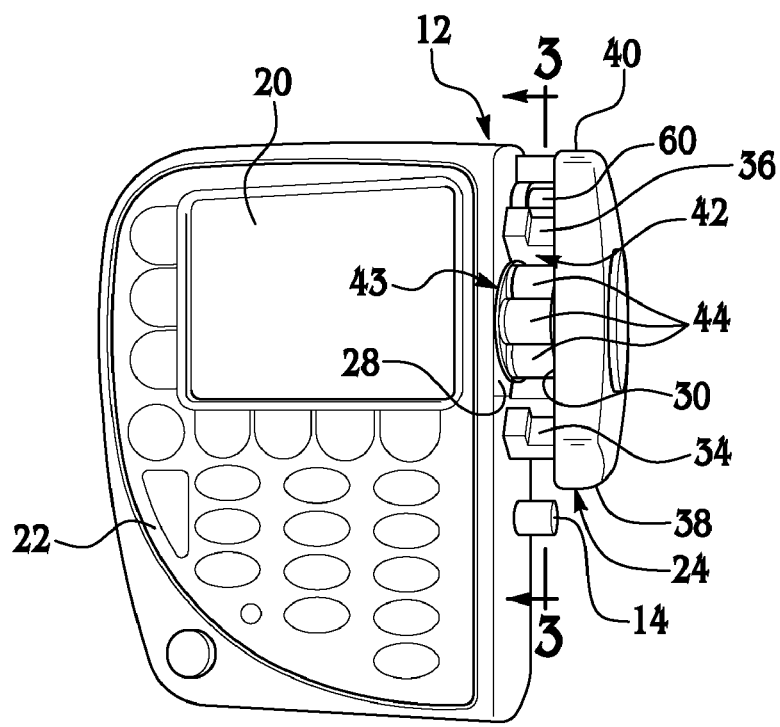
FIG. 2 is a top, perspective view of an example of a pump body for the peristaltic pump assembly of FIG. 1.

As shown in FIG. 2, the pump body 12 includes a display 20 that corresponds with a keypad 22 for inputting user information such as, for example, patient identification number, drug identification number, operator identification number, or the like. The display 20 also provides visual feedback to the operator or user of the pump 10 regarding, for example, the amount of medication administered to the patient, the flow rate of the medication, and the time for medication administration.

The pump body 12 also includes a cassette receiving portion 24 formed adjacent to the display 20. The cassette receiving portion 24 includes a partial cavity 42 defined by a floor (not shown) and two opposing walls 28, 30.

Figure 3:
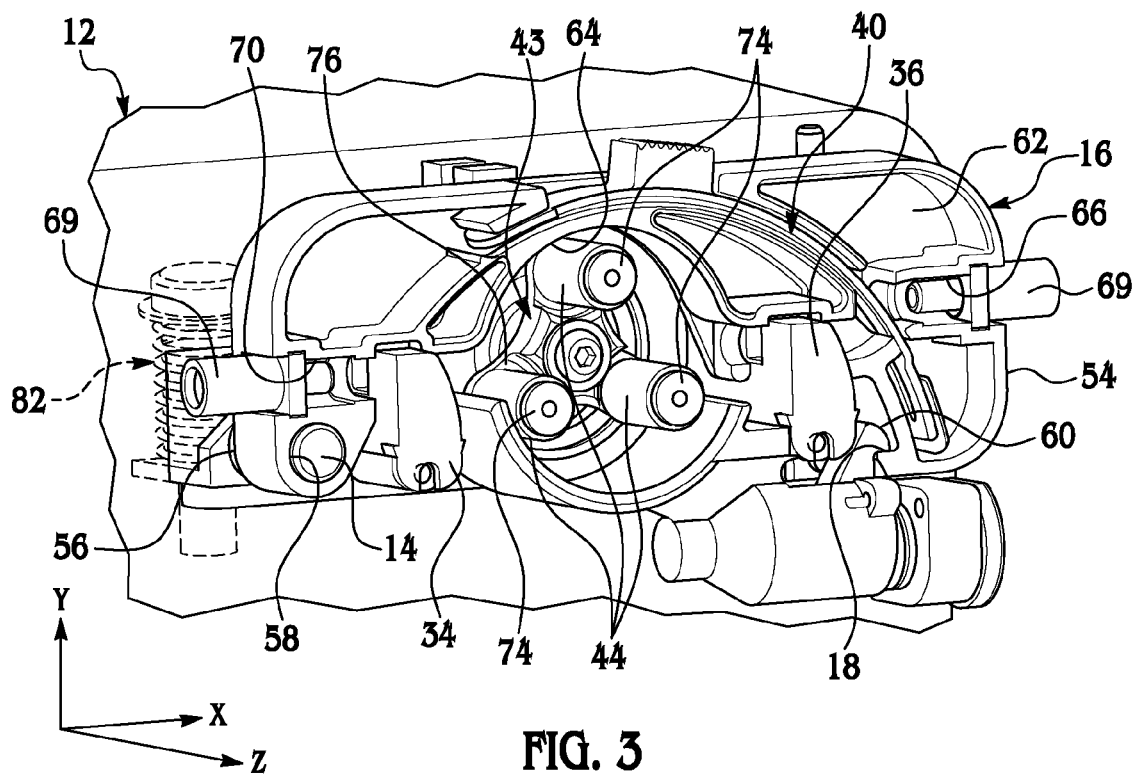
FIG. 3 is a cut-away, perspective view of the peristaltic pump assembly of FIG. 1, showing a pump body retaining feature in a closed position.

As shown in FIGS. 3 and 4, in an embodiment, a pressure sensor 36 is located upstream (e.g., near inlet end portion 40, shown in FIG. 2) in the cavity 42 of the cassette receiving portion 24. A second pressure sensor and/or an air-in-line sensor 34 is located downstream (e.g., near outlet end portion 38) in the cavity 42. It is to be understood that the pressure sensor(s) 36 may be any suitable pressure sensors, e.g., piezoelectric pressure sensors; and that the air-in-line sensors 34 may be any suitable sensors, e.g., ultrasonic air-in-line sensors. The pressure/air-in-line sensors 36, 34 are also generally shaped to complement the shape of the cassette 16. Further, the sensors 34, 36 in combination with the opposed walls 28, 30 are also generally configured to guide the cassette 16 and tubing 68 (as shown in FIG. 1) as the cassette 16 is placed or otherwise rotated into the installed position.

A roller mechanism 43 including an assembly of satellite rollers 44 is received in the partial cavity 42 and attached to a pump motor (not shown) through a bore (also not shown) formed in the wall 28. In a non-limiting example, the assembly of rollers 44 for the roller mechanism 43 are arranged in a planetary configuration, where each roller 44 is slip-fit onto a respective pin 74 supported by a yoke 76. The yoke 76 is mounted to a drive shaft (not shown), which is operated by the pump motor. As the yoke 76 rotates, the rollers 44 rotate as an assembly. It is to be understood that, since the rollers 44 are slip-fit onto the pins 74, the rollers 44 are also free to rotate individually in response to rotational forces imparted thereto from the rotational movement of the drive shaft.

The mounting pin 14 is coupled to the pump body 12 by disposing the mounting pin 14 on a pump regulator mechanism 82, and operatively disposing the regulator mechanism 82 on the pump body 12. Details of an example of the pump regulator mechanism 82 may be found in U.S. application Ser. No. 11/862,326, which is commonly owned by the Assignee of the present disclosure, and is incorporated herein by reference in its entirety. Generally, the regulator mechanism 82 allows the mounting pin 14 to slightly move in the y-direction but remains substantially stationary in the x- and z-directions (see FIG. 3). Movement in the y-direction allows the cassette 16, which is mounted to the pump body 12 via the mounting pin 14, to apply a substantially constant force to a flexible tube 68 (shown in FIG. 1), thereby occluding the tube 68 in a relatively consistent manner. It is to be understood that maintaining the mounting pin 14 in a stationary configuration with respect to the x- and z- directions, however, enables the mounting pin 14 to guide the cassette 16 when the cassette 16 is placed or rotated into and/or out of the installed position. This facilitates loading and/or removal of the cassette 16 with the pump body 12, in addition to maintaining the cassette 16 in proper operating position during pumping operation, thereby producing a desirable and suitable pumping performance of the fluid.

In an embodiment, the mounting pin 14 is cylindrically-shaped, has a substantially stout configuration, and is selected from a variety of metals including, but not limited to, aluminum and alloys thereof, steel, stainless steel, zinc and alloys thereof, and combinations thereof. In a non-limiting example, the length of the mounting pin 14 is about equal to the length of a hinge journal 58 (shown in FIG. 3) formed in the cassette 16. As will be described further hereinbelow, the cassette 16 is mounted to the pump body 12 by sliding the hinge journal 58 onto the mounting pin 14 and rotating the cassette 16 into an installed position. The hinge journal/mounting pin configuration provides a desirable bearing surface for the cassette, and facilitates proper alignment of the cassette 16 when installing it in the pump body 12.

Figure 3A:
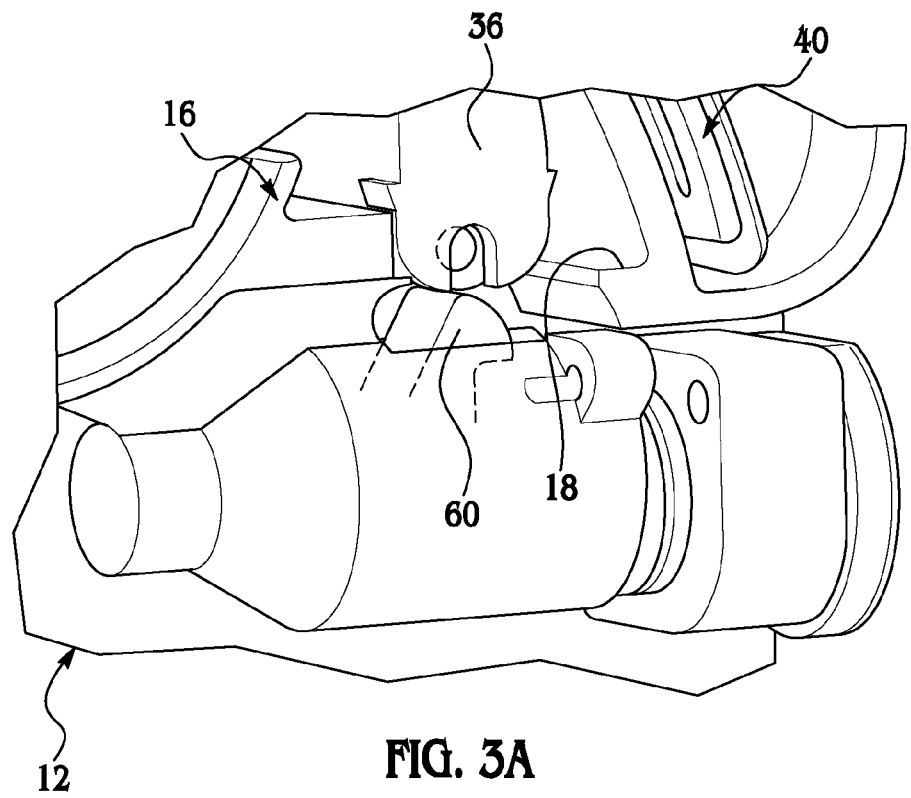
FIG. 3A is a cut-away, enlarged view of a portion of the peristaltic pump assembly of FIG. 3 showing the pump body retaining feature in an opened position.

Without being bound by any theory, it is further believed that the shape and/or conformation of the mounting pin 14, as well as the material(s) selected for the mounting pin 14, contribute to the robustness of the pin 14, which tends to lengthen the usable life thereof. It is to be understood, however, that other shapes and lengths of the mounting pin 14 and/or materials used for the mounting pin 14 may be used and still achieve the desired level of robustness of the pin 14. Formed at the other end 40 of the cassette receiving portion 24 is a pump body retaining feature 60 configured to engage the cassette retaining feature 18 to thereby lock the cassette 16 into the installed position. The retaining feature 60 is generally movable between a closed position (depicted in FIG. 3) and an opened position (depicted in FIG. 3A). As defined herein, the "closed position" refers to either the position of the retaining feature 60 at which the pump body retaining feature 60 engages the cassette retaining feature 18 when the cassette 16 is in the installed position, or refers to the position of the retaining feature 60 towards which the retaining feature 60 biases when the cassette 16 is not in the installed position. Also as defined herein, the "opened position" refers to the position of the retaining feature 60 when the retaining feature 60 is moved away from its biased position (i.e., away from the closed position).

The cassette 16 includes a body 62 including a substantially curved or rounded race 64 disposed between the opposed ends 54, 56 of the cassette 16. An inlet 66 (for the flexible or compressible tube 68) is formed into the body 62 at the first end 54, where the tube 68 fits into a guide member 69. As shown in FIG. 4, the tube 68 extends through the cassette 16, between the cassette body 62 and the pressure sensor 36 and combination pressure/air-in-line sensor 34, and into an outlet 70 formed in the cassette body 62, via another guide member 69. Further details of an example of the cassette 16 may be found in U.S. application Ser. No. 11/862,360, which is commonly owned by the Assignee of the present disclosure, and is incorporated herein by reference in its entirety.

In an embodiment, the tube 68, which is also disposable, is made of a polymeric material, non-limiting examples of which include silicones, AUTOPRENE (an opaque thermoplastic rubber with high wear resistance derived from SANTOPRENE, commercially available from Advanced Elastomer Systems, a subsidiary of ExxonMobil Chemical located in Houston, Tex.), VITON (a black fluoroelastomer with resistance to concentrated acids, solvents, ozone, radiation and temperatures up to 200° C. with good chemical compatibility, commercially available from DuPont Performance Elastomers located in Wilmington, Del.), TYGON (good chemical resistance with a clear finish, commercially available from Saint-Gobain Performance Plastics Corporation located in Akron, Ohio), PROTHANE II (a transparent, blue, polyester, polyurethane tubing with good chemical resistance, commercially available from Randolph Austin Company located in Manchaca, Tex.), and/or the like, and/or combinations thereof. The inner diameter of the tube 68 may be selected based on the desirable flow rates and the desirable viscosities of the fluid that will flow therethrough. When the cassette 16 is in the installed position, the tube 68 surrounds a portion of the assembly of rollers 44 and abuts the rounded wall 64.

When the pump 10 is operating, rotational movement of the assembly of rollers 44 pumps fluid through the tube 68 to create a pressurized flow thereof. The tube 68 compresses or otherwise occludes at a number of points in contact with the rollers 44 and the rounded race 64 on the other side thereof when the rollers 44, as an assembly and individually, are rotating. Fluid is trapped in the tube 68 between two points of occlusion (i.e., from one roller 44 to an adjacent roller 44). The trapped fluid is passed or moved through the tube 68 at a flow rate proportional to the rotational rate (rpm) of the drive shaft, and released when the tube 68 is no longer occluded by any of the rollers 44. In other words, in response to rotational movement of the rollers 44, portions of the flexible tube 68 that are in contact with the rollers 44 compress or are otherwise occluded against race 64. As a result, fluid is temporarily retained in the tube 68 between the occluded points. In this manner, fluid is urged through the tube 68 via peristaltic wave action.

The hinge journal 58 formed in the cassette body 62 is located at the end 56 of the cassette 16. The hinge journal 58 is generally formed to complement the size and shape of the mounting pin 14 to be received therein. In an embodiment, the hinge journal 58 is cylindrically-shaped and includes a length and diameter that is slightly larger than the mounting pin 14 so that the cylindrically-shaped mounting pin 14 can easily be received therein. Also, the surface of the hinge journal 58 is substantially smooth to facilitate sliding of mounting pin 14 into the hinge journal 58 when the cassette 16 is mounted on the mounting pin 14 and when the cassette 16 is rotated into the installed position.

The cassette retaining feature 18 is formed on the cassette body 62 at the other end 56. The retaining feature 18 is designed to complement or otherwise mate with the retaining feature 60 of the pump body 12. In a non-limiting example, the retaining feature 18 includes a ledge formed into the cassette body 62 and is configured to receive and hold the retaining feature 60 (e.g., a clip) when the retaining feature 60 engages the retaining feature 18.

As disclosed herein, the cassette 16 is placed into the installed position (as shown in FIG. 1) by mounting the cassette 16 to the pump body 12. This is accomplished by sliding the hinge journal 58 formed in the cassette body 62 onto the mounting pin 14. The cassette 16 is thereafter rotated on the mounting pin 14 toward the installed position. As the cassette 16 is rotated, the cassette body 62 enters the cavity 42 of the cassette receiving portion 24, while being guided by the opposed walls 28, 30, the floor, and the mounting pin 14 until the cassette body 62 (including the tube 68) substantially abuts the sensors 34, 36. When the cassette abuts the sensors 34, 36, the retaining feature 18 contacts the retaining feature 60 and the retaining feature 60 moves from the closed position, to the opened position as force is applied thereto. When the retaining feature 18 passes this point of contact, the retaining feature 60 automatically moves back to the closed position. It is to be understood that movement of the retaining feature 60 when the cassette 16 is mounted to the pump body 12 is accomplished by applying a physical force to the cassette 16. The retaining feature 60 momentarily moves to the opened position when the retaining feature 60 is pushed or otherwise forced into the opened position by the cassette 16 as the cassette 16 is placed in the installed position. The retaining feature 60 automatically snaps back into it original position, i.e., the closed position, once the cassette 16 has been placed in the installed position and engages the cassette retaining feature 18, thereby holding or securing the cassette 16 to the pump body 12.

Upon engagement of the pump body retaining feature 60 with the cassette retaining feature 18, the peristaltic pump assembly 10 also provides feedback to the operator or user. The feedback generally indicates that the cassette 16 has been properly assembled with the pump body 12. In a non-limiting example, audible feedback is achieved by a snapping or clicking sound as the retaining feature 60 snaps back into the closed position from the opened position and engages the cassette retaining feature 18 when the cassette 16 is placed in the installed position. This snapping or clicking sound enables the operator to ensure that the cassette 16 has been mounted or otherwise assembled properly, and that pumping of fluid may commence. In another non-limiting example, tactile feedback is achieved when the retaining feature 60 engages the retaining feature 18 and movement of the cassette 16 thereafter cannot occur.

In an embodiment, and with reference now to FIGS. 5 and 6, the cassette 16 is released from or otherwise rotated out of the installed position by disengaging the pump body retaining feature 60 from the cassette retaining feature 18. Disengagement is achieved when the retaining feature 60 is moved to the opened position, thereby releasing the retaining feature 18. In an embodiment, the retaining feature 60 is moved to the opened position by actuating a release device 72. In a non-limiting example, the release device 72 is a button, whereby when the button is pushed the retaining feature 60 is moved from the closed position to the opened position. The cassette 16 is thereafter rotated about the mounting pin 14 out of the assembled position and slidingly disengaged from the mounting pin 14.

It is to be understood that the term "couple/coupled" or the like is broadly defined herein to encompass a variety of divergent connection arrangements and assembly techniques. These arrangements and techniques include, but are not limited to (1) the direct coupling between one component and another component with no intervening components therebetween; and (2) the coupling of one component and another component with one or more components therebetween, provided that the one component being "coupled to" the other component is somehow operatively coupled to the other component (notwithstanding the presence of one or more additional components therebetween).

While several embodiments have been described in detail, it will be apparent to those skilled in the art that the disclosed embodiments may be modified. Therefore, the foregoing description is to be considered exemplary rather than limiting.

What is claimed is:

1. A method of installing a cassette having a tube inlet and a tube outlet in a pump body, comprising:
   sliding the cassette onto a mounting pin included in a pump body; and
   rotating the cassette about the mounting pin until a cassette retaining feature engages a pump body retaining feature, thereby installing the cassette in the pump body, wherein the pump body is configured to allow movement of the mounting pin relative to the pump body along a linear path that is perpendicular to the mounting pin axis when the cassette is in the installed position.

2. The method as defined in claim 1, further comprising generating audible feedback, tactile feedback, or combinations thereof when the cassette retaining feature engages the pump body retaining feature, thereby indicating that the cassette has been rotated into an installed position.

3. The method as defined in claim 1, further comprising moving the pump body retaining feature from a closed position to an opened position and back to the closed position when the cassette retaining feature engages the pump body retaining feature.

4. The method as defined in claim 1 wherein the mounting pin is slidably received in a hinge journal formed in the cassette.

5. The method as defined in claim 1 wherein the pump body is configured to guide the cassette as the cassette is rotated into the installed position.

6. A method of removing a cassette having a tube inlet and a tube outlet from a pump body having a mounting pin, the pump body configured to allow movement of the mounting pin relative to the pump body along a linear path that is perpendicular to the mounting pin axis when the cassette is in the installed position, the method comprising:
   disengaging a cassette retaining feature from a pump body retaining feature, the pump body retaining feature being disposed in the pump body, the pump body including the cassette installed therein;
   rotating the cassette about the mounting pin out of an installed position; and
   sliding the cassette off of the mounting pin, thereby removing the cassette from the pump body.

7. The method as defined in claim 6 wherein disengaging is accomplished by actuating a release device.

8. The method as defined in claim 7 wherein the release device is a button.

9. The method as defined in claim 6 wherein disengaging is further accomplished by moving the pump body retaining feature from a closed position to an opened position.

* * * * *